(12) United States Patent
Nair et al.

(10) Patent No.: US 9,233,890 B2
(45) Date of Patent: Jan. 12, 2016

(54) PROCESS FOR PRODUCING PHENOL

(71) Applicant: ExxonMobil Chemical Patents Inc., Baytown, TX (US)

(72) Inventors: Hari Nair, Houston, TX (US); Christopher L. Becker, Manhattan, KS (US); Ryan A. Sothen, Houston, TX (US); Charles Morris Smith, Princeton, NJ (US); Tan-Jen Chen, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/402,273

(22) PCT Filed: Jul. 9, 2013

(86) PCT No.: PCT/US2013/049717
§ 371 (c)(1),
(2) Date: Nov. 19, 2014

(87) PCT Pub. No.: WO2014/014708
PCT Pub. Date: Jan. 23, 2014

(65) Prior Publication Data
US 2015/0158788 A1    Jun. 11, 2015

Related U.S. Application Data

(60) Provisional application No. 61/674,019, filed on Jul. 20, 2012.

(30) Foreign Application Priority Data

Sep. 12, 2012   (EP) .................................... 12184047

(51) Int. Cl.
| | | |
|---|---|---|
| C07C 45/53 | (2006.01) |
| C07C 37/08 | (2006.01) |
| C07C 2/66 | (2006.01) |
| C07C 2/74 | (2006.01) |
| C07C 13/28 | (2006.01) |
| C07C 7/12 | (2006.01) |
| C07C 7/13 | (2006.01) |
| C07C 37/50 | (2006.01) |
| C07C 45/00 | (2006.01) |
| C07C 407/00 | (2006.01) |

(52) U.S. Cl.
CPC ... *C07C 2/74* (2013.01); *C07C 7/12* (2013.01); *C07C 7/13* (2013.01); *C07C 13/28* (2013.01); *C07C 37/08* (2013.01); *C07C 37/50* (2013.01); *C07C 45/00* (2013.01); *C07C 45/53* (2013.01); *C07C 407/00* (2013.01); *C07C 2101/14* (2013.01); *C07C 2529/70* (2013.01)

(58) Field of Classification Search
CPC ............ C07C 45/53; C07C 37/08; C07C 2/66
USPC .......................... 568/342, 347, 798; 585/467
See application file for complete search history.

(56) References Cited

U.S. PATENT DOCUMENTS

| | | | |
|---|---|---|---|
| 4,247,729 A * | 1/1981 | Takahashi et al. ............ 585/483 |
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,077,498 A | 6/2000 | Diaz Cabañas et al. |
| 6,756,030 B1 | 6/2004 | Rohde et al. |
| 2011/0037022 A1* | 2/2011 | Dakka et al. .............. 252/182.31 |
| 2013/0202522 A1* | 8/2013 | Chen et al. ................. 423/648.1 |

FOREIGN PATENT DOCUMENTS

| | | |
|---|---|---|
| EP | 0 293 032 | 11/1988 |
| WO | WO 97/17290 | 5/1997 |
| WO | WO 2009/131769 | 10/2009 |
| WO | WO 2011/146167 | 11/2011 |
| WO | WO2011/146167 | * 11/2011 |

* cited by examiner

*Primary Examiner* — Sikarl Witherspoon
(74) *Attorney, Agent, or Firm* — Siwen Chen; Stephen A. Baehl

(57) ABSTRACT

Provided is a process for producing cyclohexylbenzene, in which a benzene feed stream is subjected to each of the following treatment steps: treating the feed stream with at least one adsorbent and fractionating the feed stream to remove components having a different boiling point than benzene. The treatment steps are carried out in any order and produce a treated benzene feed stream. The treated benzene feed stream is then contacted with hydrogen in the presence of a hydroalkylation catalyst in a hydroalkylation unit under conditions effective to produce a reaction product containing cyclohexylbenzene.

16 Claims, 5 Drawing Sheets

PROCESS FOR PRODUCING PHENOL

PRIORITY CLAIM

Cross Reference to Related Applications

The application is a national stage application of International Application No. PCT/US2013/049717, filed Jul. 9, 2013, U.S. Provisional Application No. 61/674,019 filed Jul. 20, 2012, and European Application No. 12184047.4 filed Sep. 12, 2012, the disclosures of which are fully incorporated by reference herein in their entireties.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogenous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is via benzene hydroalkylation in which benzene is contacted with hydrogen in the presence of a catalyst such that part of the benzene is converted into cyclohexene which then reacts with the remaining benzene to produce the desired cyclohexylbenzene. One such method is disclosed in U.S. Pat. No. 6,037,513, in which the catalyst comprises a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product in roughly equimolar amounts.

There are, however, a number of problems associated with producing phenol via cyclohexylbenzene rather than the cumene-based Hock process. One such problem is that, even with the most selective catalysts, the process converts only a portion of the benzene feed per pass and the reaction product inherently contains a non-negligible amount of cyclohexane, which is normally converted into benzene at a downstream step. Thus, a viable commercial benzene hydroalkylation plant will likely include recycle of both unreacted benzene from the primary hydroalkylation step but also of benzene produced in downstream processing steps. This leads to an additional problem in that both sources of benzene tend to contain impurities that can adversely affect the hydroalkylation catalyst. For example, deleterious impurities in fresh benzene include water, light aliphatics, olefins, diolefins, styrene, toluene and other aromatics, oxygenated organic compounds, sulfur-containing compounds, nitrogen-containing compounds, and oligomeric compounds. Impurities in the recycle benzene that may affect the hydroalkylation catalyst include toluene, biphenyl, and light aliphatics/olefins/diolefins.

International patent application publication No. WO 2011/146167 A2 provides a general description of the influence of impurities in the benzene and, more particularly, the hydrogen employed in benzene hydroalkylation processes. In the case of benzene, the relevant impurities are said to include nitrogen and sulfur compounds and are removed by treatment with adsorbents, such as molecular sieves.

However, in view of the wide range of potential impurities encountered in a commercial setting, there remains a need for an improved process for removing the impurities from the fresh and recycle benzene feed steams to benzene hydroalkylation units and the present invention seeks to address this need.

SUMMARY

According to one aspect of the invention, there is provided a process for producing cyclohexylbenzene, the process comprising:
(a) subjecting a benzene feed stream to each of the following treatment steps:
   (i) treating the feed stream with at least one adsorbent; and
   (ii) fractionating the feed stream to remove at least some components having a different boiling point than benzene, wherein said treatment steps (i) and (ii) are carried out in any order and produce a treated benzene feed stream; and
(b) contacting the treated benzene feed stream with hydrogen in the presence of a catalyst in a hydroalkylation unit under conditions effective to produce a reaction product containing cyclohexylbenzene.

In certain embodiments, said fractionating step (ii) removes at least some components having a lower boiling point than benzene and at least some components having a higher boiling point than benzene.

Conveniently, the benzene feed stream comprises fresh and recycled benzene. Alternatively, the benzene feed stream comprises fresh benzene and a further recycled benzene stream is mixed with the fresh benzene stream after at least part of said treating step (i) but before said fractionating step (ii). In one embodiment, the recycled benzene comprises unreacted benzene in the reaction effluent from step (b). In another embodiment, the reaction effluent from step (b) comprises cyclohexane and said recycled benzene comprises benzene produced by dehydrogenation of said cyclohexane.

In certain embodiments, said at least one adsorbent comprises at least one of an acidic clay, a metal and/or metal oxide and a molecular sieve. In one embodiment, the at least one adsorbent comprises a molecular sieve having a pore size less than 6 Å and/or a molecular sieve having a pore size equal to or greater than 6 Å. Conveniently, the treating step (i) comprises passing the feed stream through a first sorbent bed comprising a molecular sieve having a pore size less than 6 Å and passing the feed stream through a second sorbent bed comprising a molecular sieve having a pore size equal to or greater than 6 Å. Preferably, the feed stream is passed through the first sorbent bed before being passed through the second sorbent bed.

In certain embodiments, the at least one adsorbent is contained in at least one sorbent bed, which may be housed in the hydroalkylation unit upstream of the bifunctional catalyst, in a fractionation column used to effect the fractionating step (ii) and/or in a container separate from the hydroalkylation unit and the fractionation column(s) used to effect the fractionating step (ii).

In a further aspect, the invention resides in a process for producing phenol, the process comprising:
(a) subjecting a benzene feed stream to each of the following treatment steps:
  (i) treating the feed stream with at least one adsorbent; and
  (ii) fractionating the feed stream to remove components having a different boiling point than benzene,
wherein said treatment steps (i) and (ii) are carried out in any order and produce a treated benzene feed stream;
(b) contacting the treated benzene feed stream with hydrogen in the presence of a catalyst in a hydroalkylation unit under conditions effective to produce a reaction product containing cyclohexylbenzene;
(c) oxidizing at least part of the cyclohexylbenzene from (b) to produce cyclohexylbenzene hydroperoxide; and
(d) cleaving at least part of the cyclohexylbenzene hydroperoxide to produce phenol and cyclohexanone.

DETAILED DESCRIPTION OF THE EMBODIMENTS

Figure 1:
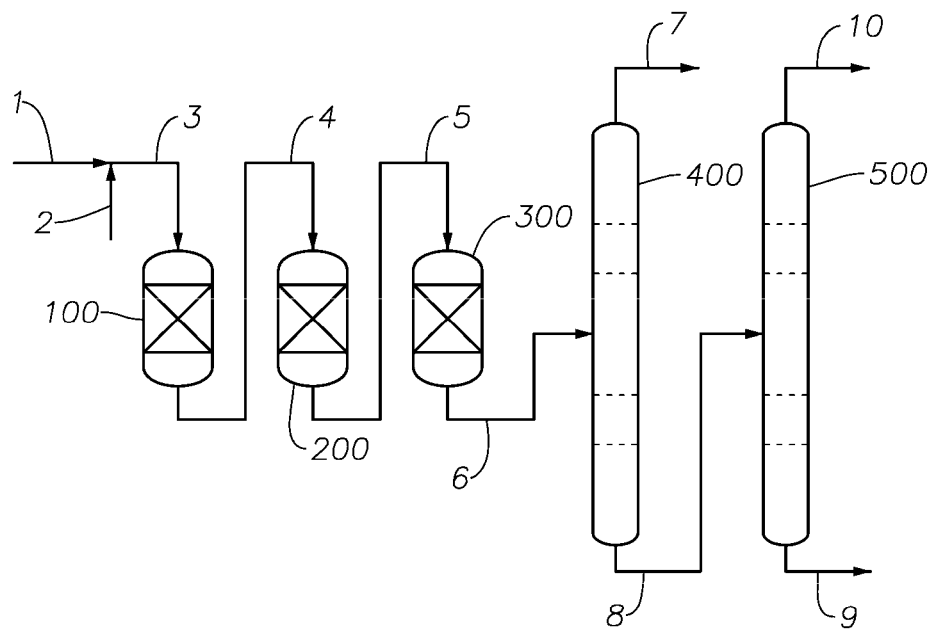
FIGS. 1 to 9 are schematic diagrams of nine different embodiments, respectively, of the present process for producing cyclohexylbenzene.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw material fed into the process earlier in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "an adsorbent" include embodiments where one, two, or more adsorbents are used, unless specified to the contrary or the context clearly indicates that only one adsorbent is used.

Described herein is process in which a benzene feed stream is contacted with hydrogen in a hydroalkylation unit in the presence of a hydroalkylation catalyst to produce cyclohexylbenzene. The benzene feed stream comprises fresh benzene added to the system normally together with recycle benzene separated from the hydroalkylation unit effluent and recycle benzene produced by dehydrogenation of cyclohexane generated as a by-product of the hydroalkylation reaction. To protect the hydroalkylation catalyst from deleterious impurities present in the fresh and recycle benzene, part or all of the benzene feed stream is subjected to a treatment process comprising (i) treating the feed stream with at least one adsorbent; and (ii) fractionating the feed stream to remove at least some of the components having a different boiling point than benzene. The treatment steps (i) and (ii) can be carried out in any order.

In one preferred embodiment, the present process forms part of an integrated process for producing phenol from benzene in which the cyclohexylbenzene produced in the benzene hydroalkylation reaction is oxidized to produce cyclohexylbenzene hydroperoxide and the hydroperoxide is cleaved to produce phenol and cyclohexanone. The ensuing description will therefore focus on this integrated process.

Pretreatment of the Benzene Feed

Commercially available benzene feeds used as the fresh or make-up benzene in the hydroalkylation process may contain contaminants such as water, light aliphatics, olefins, diolefins, styrene, toluene and other aromatics, oxygenated organic compounds, sulfur-containing compounds, nitrogen-containing compounds, and oligomeric compounds. Exemplary impurities in the recycle benzene that may affect the hydroalkylation catalyst include toluene, biphenyl, and light ($C_5$-) aliphatics/olefins/diolefins.

In certain embodiments, it is desirable that the total feed to the hydroalkylation step contains less than 1000 ppm, such as less than 500 ppm, for example less than 100 ppm or less than 20 ppm, water. In addition, the total feed may contain less than 100 ppm, such as less than 30 ppm or less than 20 ppm, for example less than 3 ppm, less than 1 ppm, or free of, sulfur and less than 20 ppm, such as less than 10 ppm, or less than 1 ppm, for example less than 0.1 ppm or free of, nitrogen. In the case of light aliphatics, olefins, diolefins, styrene, toluene and other aromatics, oxygenated organic compounds, and oligomeric compounds, the level of each impurity in the feed is desirably less than 1000 ppm, such as less than 100 ppm, for example less than 10 ppm.

Sulfur and nitrogen-containing compounds are especially deleterious impurities with respect to the hydroalkylation catalyst. The main sources of sulfur-containing compounds in the feed to the hydroalkylation unit are from impurities in hydrocarbon feedstocks in the chemical plant (e.g., thiophene), extraction solvents used in the chemical plant (NFM, sulfolane), and additives used. Similarly, the main sources of nitrogen-containing compounds in the feed to the hydroalkylation unit are from impurities in hydrocarbon feedstocks in the chemical plant (e.g., coal tar benzene contains nitrogen compounds) and additives used (corrosion inhibitors or by-products from the corrosion inhibitors).

As noted above, protection of the hydroalkylation catalyst from the deleterious impurities present in the fresh and recycle benzene includes treating the benzene with one or more adsorbent materials. Suitable adsorbent materials include acidic clays, metals and metal oxides, and acidic zeolites with pore sizes ranging between 3 and 9 Å. The adsorbent materials are conveniently divided into three classes depending on the impurities being targeted. The first class of materials (Class I) comprises acidic zeolites (i.e., molecular sieves) having a pores size less than 6 Å (e.g., zeolite 3A, zeolite 4A, zeolite 5A, ZSM-5) to selectively remove small molecules, including water. The second class of materials (Class II) comprise acidic clays or acidic zeolites (i.e., molecular sieves) having a pores size equal to or greater than 6 Å (e.g., zeolite 13X, MCM-22, MCM-36, MCM-49, MCM-56, ITQ-1, ITQ-2, PSH-3, SSZ-25, zeolite beta, mordenite, zeolite omega, US-Y, ZSM-5, Selexsorb® CDO/Selexsorb® CDX). Class II materials are effective to remove some nitrogen and sulfur-containing compounds, styrene, and some oxygenated organic compounds. The third class of materials (Class III) is primarily used for removal of nitrogen- and sulfur-containing compounds that have an effect on the metal functionality of the catalyst. Class III materials include metals, such as, nickel and palladium and metal oxides, such as alumina (e.g., Selexsorb® CDX), zinc oxide, and titanium oxide. Class III materials can operate at ambient temperatures or elevated temperatures (e.g., ZnO) for reactive separations. The operating conditions of the Class III materials used may help dictate where such materials would be used in the pretreatment scheme.

In certain embodiments, the adsorbent materials are mounted in one or more adsorbent beds that can be arranged in parallel or in series. One, two, or all three of the classes of materials may be used in any order, depending on the nature of the feed. Single (stacked/layered) or multiple beds using a single adsorbent or multiple adsorbents of different classes may also be used. Different classes of materials may also be mixed in a single adsorption bed, if deemed appropriate for the location of the adsorption bed. It may be desirable to operate the adsorption beds at temperatures higher than room temperature (e.g., between 30° C. and 220° C.) to facilitate removal of olefins and/or styrenes and/or nitrogen and/or sulfur-containing compounds, by reacting them with other compounds and removing them. Beds containing smaller pore materials (i.e., Class I) are desirably operated at temperatures less than 200° C., for example, below 100° C., to facilitate removal of smaller compounds by adsorption.

As further noted above, protection of the hydroalkylation catalyst from the deleterious impurities present in the fresh and recycle benzene, also includes fractionating (i.e., distilling) the feed stream to remove at least some of the components in the feed stream having a boiling point different from that of benzene. Generally, the fractionation includes removing components having a lower boiling point than benzene (e.g., hexane, pentane, etc.) and removing components having a higher boiling point than benzene (e.g., cyclohexane, toluene, thiophene, biphenyl, etc.). One or both of these separations may be applicable for a given location in the pretreatment process and can be accomplished in either the same fractionation column or separate columns.

The precise arrangement of the pretreatment techniques depends on the feed source of benzene and the nature and amount of impurities that may be present. For example, where larger amounts of impurities are present, it may be desirable to affect at least one fractionation step before passage of the feed through an adsorbent.

Hydroalkylation Reaction

The resultant purified benzene feed is then contacted with hydrogen to produce cyclohexylbenzene according to the following reaction:

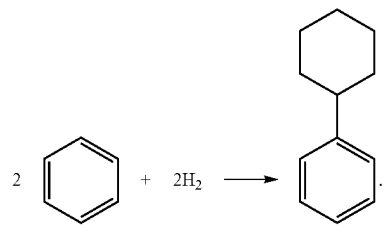 [SMILES: c1ccccc1 ; c1ccc(C2CCCCC2)cc1]

The reaction is generally conducted in the presence of a bifunctional catalyst having a hydrogenation component which catalyzes the selective hydrogenation of benzene to produce cyclohexene and an alkylation component which catalyzes alkylation of benzene with the in-situ produced cyclohexene to produce cyclohexylbenzene.

Any known hydrogenation metal can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between about 0.05 wt % and about 10 wt %, such as between about 0.1 wt % and about 5 wt %, of the catalyst.

In certain embodiments, the alkylation component of the catalyst is desirably a molecular sieve such as a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954, 325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO 97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49; (b) MCM-56; and (c) isotypes of MCM-49 and MCM-56, such as ITQ-2.

In one embodiment, the MCM-22 family molecular sieve is an aluminosilicate and the amount of hydrogenation metal present on the catalyst is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example, at least 75 wt %, and even substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. In certain embodiments, the catalyst composite is produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

In addition to the benzene and hydrogen, a diluent, which is substantially inert under hydroalkylation conditions, may be supplied to the hydroalkylation reaction. In certain embodiments, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

Although the hydroalkylation reaction using an MCM-22 family zeolite catalyst is highly selective towards cyclohexylbenzene, the effluent from the hydroalkylation reaction will inevitably contain some cyclohexane as a by-product. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst desirably comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. In certain embodiments, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. In certain embodiments, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 to 50 hr$^{-1}$, and a hydrogen to hydrocarbon feed molar ratio of about 0 to about 20.

Production of Phenol

In one preferred embodiment, the cyclohexylbenzene product of the benzene hydroalkylation reaction described above is used to produce phenol and cyclohexanone. In such an embodiment, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to remove particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N''-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other absorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other absorbable components, and provide an oxidation composition reduced in oxidation catalyst or other absorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Cleavage of the cyclohexyl-1-phenyl-1-hydroperoxide produced in the oxidation step into phenol and cyclohexanone is conducted in the presence of an acid catalyst.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and no greater than 3000 wppm, or at least 150 wppm to and no greater than 2000 wppm of the acid catalyst, or at least 300 wppm to and no greater than 1500 wppm of the acid catalyst, based upon total weight of the cleavage reaction mixture.

In other embodiments, a heterogeneous acid catalyst is employed for the cleavage reaction, such as molecular sieve, and, in particular, a molecular sieve having a pore size in excess of 7 Å. Examples of suitable molecular sieves include zeolite beta, zeolite Y, zeolite X, ZSM-12 and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The product of the cleavage reaction is generally a substantially equimolar mixture of phenol and cyclohexanone.

The invention will now be more particularly described with reference to the accompanying drawings, which illustrate nine different configurations of the present benzene purification and hydroalkylation process.

A basic configuration of the present benzene pretreatment process is shown in FIG. 1, in which a fresh benzene stream 1 is mixed with a recycled benzene stream 2 to obtain a mixed benzene stream 3. The mixed benzene stream 3 is fed to a first adsorber 100 to produce a first treated stream 4. The first treated stream 4 is then fed to a second adsorber 200 to produce a second treated stream 5, which is then fed to a third adsorber 300 to produce a third treated stream 6. Adsorbers 100, 200, 300 may contain Class I materials, Class II materials, or Class III materials in any order. Moreover, adsorbers 100, 200, 300 may contain a single adsorbent, a single class of materials (i.e., more than one material belonging to a single class), or multiple classes of material. The adsorbers may be heated to temperatures higher than ambient. In an embodiment, benzene is treated with Class I materials before Class II materials to ensure that water and other smaller poisons do not interfere with the operation of the larger pore materials. The third treated benzene stream 6 from the adsorber 300 is then fed to distillation columns 400, 500. In FIG. 1, an overhead stream 7 containing contaminants having a lower boiling point than benzene is removed from the benzene stream 6 in distillation column 400 to produce a topped benzene stream 8. The topped benzene stream 8 is then fed to the distillation column 500 where a bottoms stream 9 containing contaminants having a higher boiling point than benzene is removed to produce a hydroalkylation feed stream 10.

Figure 2:
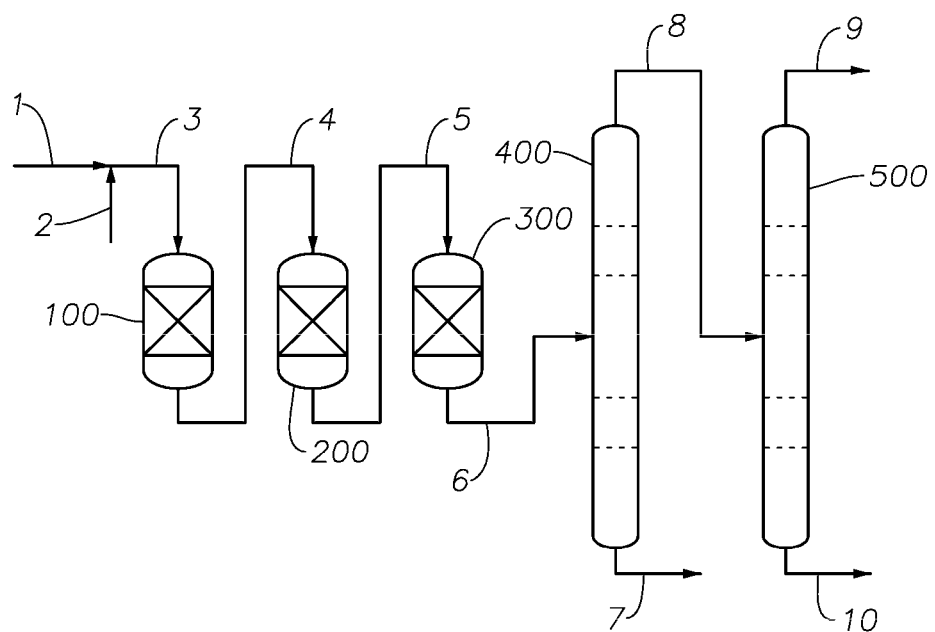

The order of distillation columns 400, 500 may be reversed to produce an embodiment shown in FIG. 2. In particular, a stream 7 containing higher boiling components is removed from treated benzene stream 6 in distillation column 400 to produce a tailed benzene stream 8. A stream 9 containing lower boiling contaminants is removed from the tailed benzene stream 8 in distillation column 500 to produce hydroalkylation feed stream 10.

Figure 3:
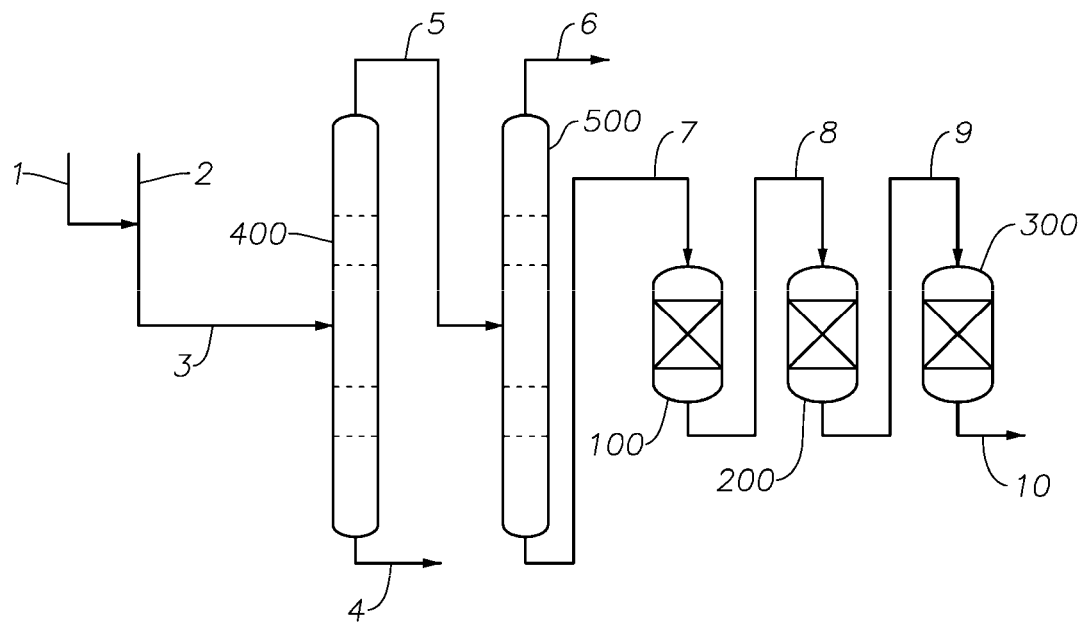

In some cases, it may be advantageous to distill impurities out first and then pass the benzene through the adsorbers. FIG. 3 provides an embodiment in which distillation is followed by adsorption. Distillation columns 400, 500 are used to tail and top mixed benzene stream 3 before passing through adsorbers 100, 200, 300. The distillation columns may be in the reverse order, i.e., topped and then tailed (see FIG. 1).

Figure 4:
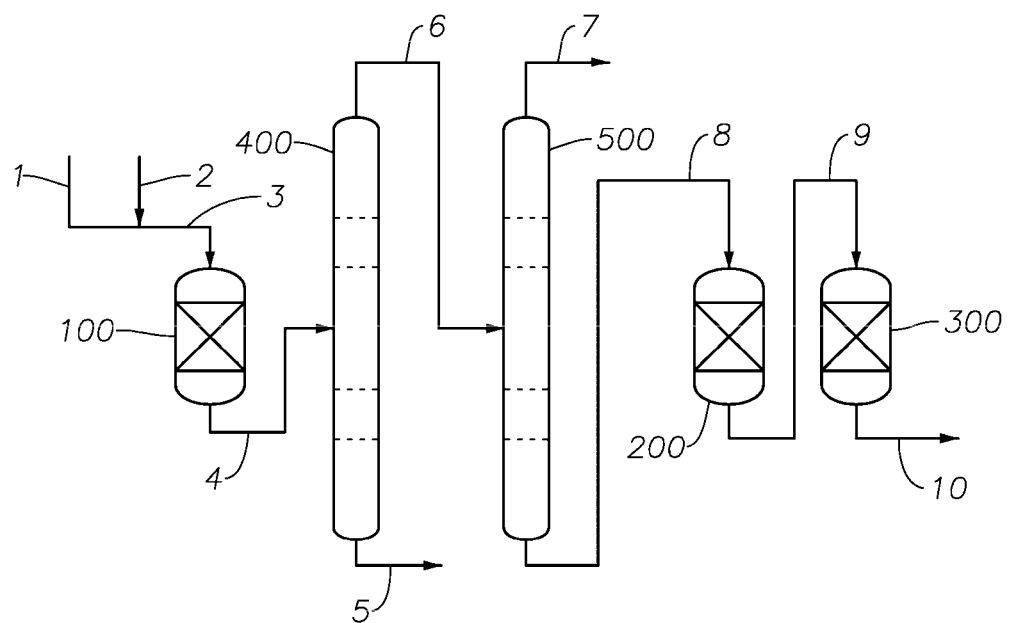
Figure 5:
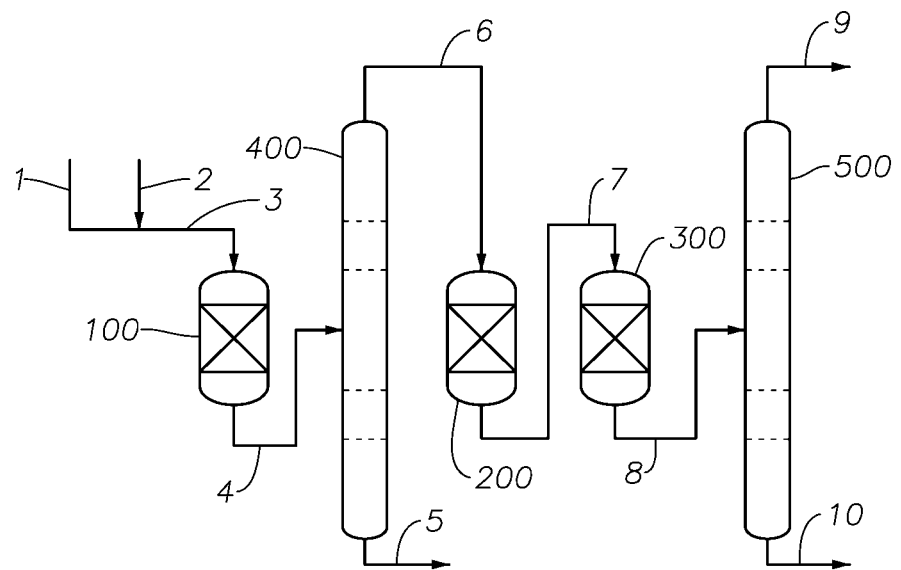

In certain embodiments, one or more of the adsorbers may be operated at elevated temperatures. In cases where only one adsorber needs to be operated at elevated temperatures, there may be an advantage in performing distillation between the adsorbers (see FIGS. 4 and 5). Both distillation columns (see FIG. 4) or one distillation column (see FIG. 5) could be located between the adsorbers, with the later adsorber(s) operated at elevated temperatures (30° C. to 220° C.). While FIGS. 4 and 5 both show a single adsorber prior to the first distillation column, more than one adsorber may be present prior to the first distillation column. Further, each adsorber may be separated by a distillation column.

Figure 6:
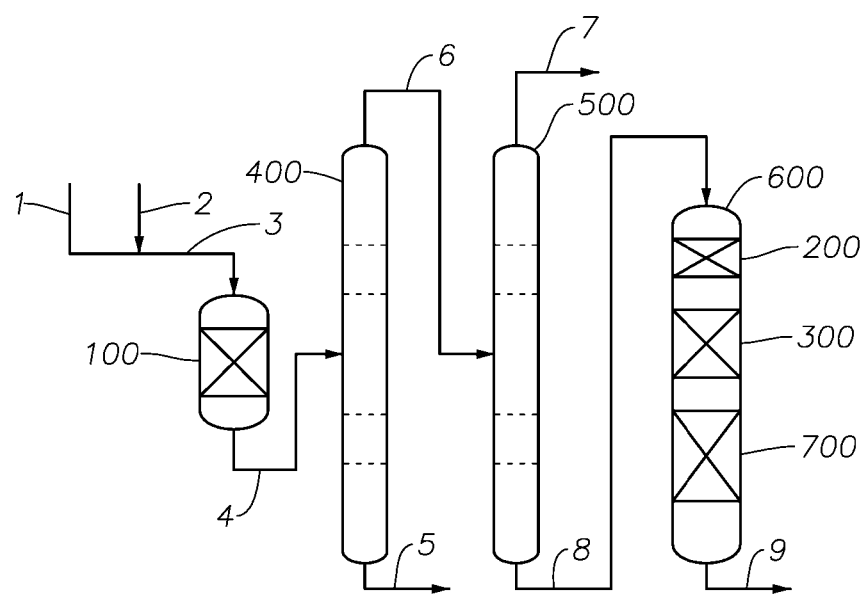

In situations where one or more of the adsorbers is to be operated at elevated temperatures and immediately preceding the hydroalkylation reactor, the adsorber(s) may be included in the hydroalkylation reactor 600, which includes hydroalkylation catalyst bed 700 (see FIG. 6), so as to reduce costs. More than one adsorption bed may be included in the hydroalkylation reactor prior to the hydroalkylation catalyst bed.

Figure 7:
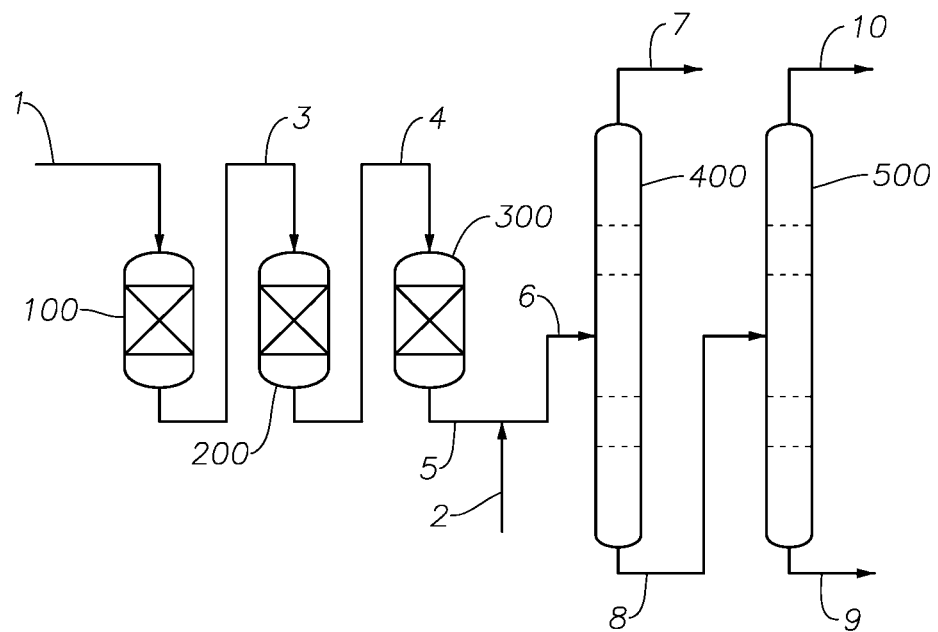
Figure 8:
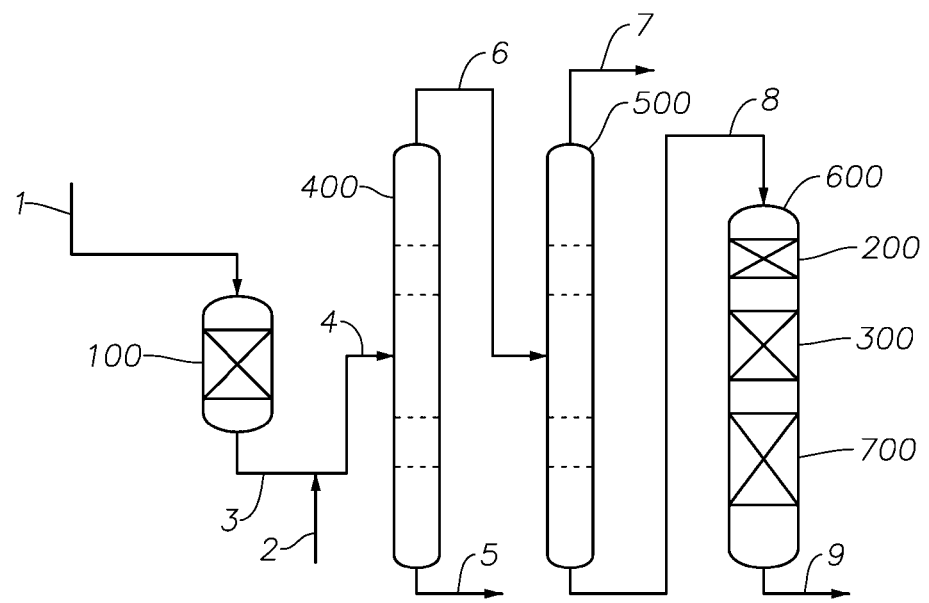

Since benzene recycled from the process is expected to be lacking in at least some contaminants (e.g., water), the recycle benzene may be introduced in a location different from the fresh benzene. For example, in FIG. 7, while the basic configuration of FIG. 1 is substantially maintained, the recycled benzene stream 2 is introduced after adsorbers 100, 200, 300, which allows for a reduction in size of the adsorbers. Introduction of the recycled benzene after the adsorbers can be done in all the embodiments outlined above. FIG. 8 shows an embodiment similar to that of FIG. 6, except that recycled benzene stream 2 is introduced after the first adsorber 100 (i.e., recycled benzene stream 2 is not processed in the first adsorber 100). Depending on the impurities seen in the recycled benzene, any of the treatment steps may be skipped.

Figure 9:
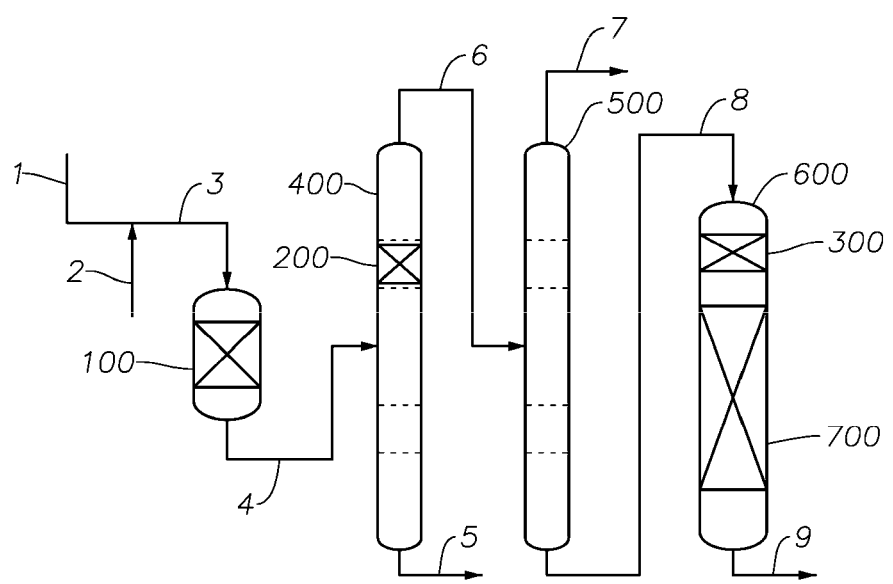

FIG. 9 shows an embodiment in which one adsorption bed 200 is located in the first distillation column 400. Heavies will come out at the bottom 5 of the distillation column 400. One of the other adsorbers 100 is located before the distillation columns 400, 500, while the other adsorption bed 300 is located in the hydroalkylation reactor 600 (which includes hydroalkylation catalyst bed 700).

While all the embodiments shown in the figures comprises at most three adsorbent beds and at most two fractionation columns, one having ordinary skill in the art should readily appreciate that, in the light of the teachings of the present disclosure, one may use more than three adsorbent beds, housed in any number of containers, and more than two fractionation columns, to achieved the intended purification purpose.

The presently disclosed process provides great flexibility in using the described adsorbents and distillations in any form possible; the specific scheme will depend on where the process is to be performed.

While various embodiments have been described, it is to be understood that variations and modifications may be resorted to as will be apparent to those skilled in the art. Such variations and modifications are to be considered within the purview and scope of the claims appended hereto.

The invention claimed is:

1. A process for producing cyclohexylbenzene, the process comprising:
   (i) treating a fresh benzene feed stream with at least one adsorbent to form a treated fresh benzene stream;
   (ii) mixing a recycled benzene stream with the treated fresh benzene stream to form a mixed benzene stream;
   (iii) fractionating the mixed benzene stream to remove at least some components having a different boiling point than benzene, thereby forming a treated benzene feed stream; and
   (iv) contacting the treated benzene feed stream with hydrogen in the presence of a catalyst in a hydroalkylation unit under conditions effective to produce a reaction product containing cyclohexylbenzene.

2. The process of claim 1, wherein said recycled benzene stream comprises unreacted benzene in the reaction product from step (iv).

3. The process of claim 2, wherein the reaction product from step (iv) comprises cyclohexane and said recycled benzene stream further comprises benzene produced by dehydrogenation of said cyclohexane.

4. The process of claim 1, wherein said at least one adsorbent comprises at least one of an acidic clay, a metal and/or metal oxide and a molecular sieve.

5. The process of claim 1, wherein said at least one adsorbent comprises a molecular sieve having a pore size in a range from 0.5 Å to less than 6 Å.

6. The process of claim 1, wherein said at least one adsorbent comprises a molecular sieve having a pore size in a range from 6 Å to 15 Å.

7. The process of claim 1, wherein said treating step (i) comprises passing the fresh benzene feed stream through a first sorbent bed comprising a molecular sieve having a pore size in a range from 0.5 Å to less than 6 Å and passing the fresh benzene feed stream through a second sorbent bed comprising a molecular sieve having a pore size in a range from 6 Å to 15 Å.

8. The process of claim 7, wherein the fresh benzene feed stream is passed through the first sorbent bed before being passed through the second sorbent bed.

9. The process of claim 1, wherein said at least one adsorbent is contained in at least one sorbent bed.

10. The process of claim 1, wherein said fractionating step (iii) removes at least some components having a lower boiling point than benzene and at least some components having a higher boiling point than benzene.

11. The process of claim 1, wherein said fractionating step (iii) is conducted in at least two fractionation columns.

12. The process of claim 1, wherein said fractionating step (iii) is conducted in a single fractionation column.

13. The process of claim 1, wherein the treated benzene feed stream meets at least one of the following conditions:
   (i) having a concentration of nitrogen of at most 20 ppm;
   (ii) having a concentration of sulfur of at most 100 ppm; and
   (iii) having a $H_2O$ concentration of at most 1,000 ppm.

14. The process of claim 1, wherein the catalyst in (iv) comprises at least one molecular sieve and at least one hydrogenation metal.

15. The process of claim 14, wherein the at least one molecular sieve is selected from zeolite beta, mordenite, zeolite X, zeolite Y and a molecular sieve of the MCM-22 family.

16. The process of claim 1 and further comprising:
   (v) oxidizing at least part of the cyclohexylbenzene from (iv) to produce cyclohexylbenzene hydroperoxide; and
   (vi) cleaving at least part of the cyclohexylbenzene hydroperoxide to produce phenol and cyclohexanone.

* * * * *